United States Patent
Jenkins et al.

(10) Patent No.: US 6,358,056 B1
(45) Date of Patent: Mar. 19, 2002

(54) METHOD FOR ADAPTIVELY TRAINING HUMANS TO DISCRIMINATE BETWEEN FREQUENCY SWEEPS COMMON IN SPOKEN LANGUAGE

(75) Inventors: William M. Jenkins, Pacifica; Michael M. Merzenich, San Francisco; Steven L. Miller, Pacifica; Bret E. Peterson, Lafayette, all of CA (US); Paula Tallal, Lumberville, PA (US)

(73) Assignee: Scientific Learning Corporation, Oakland, CA (US)

( * ) Notice: Subject to any disclaimer, the term of this patent is extended or adjusted under 35 U.S.C. 154(b) by 105 days.

(21) Appl. No.: 09/598,575

(22) Filed: Jun. 21, 2000

Related U.S. Application Data

(60) Division of application No. 09/098,199, filed on Jun. 16, 1998, now Pat. No. 6,210,166, which is a continuation-in-part of application No. 08/982,189, filed on Dec. 17, 1997, now Pat. No. 5,927,988.

(51) Int. Cl.[7] ............................. G09B 9/00; G09B 23/00
(52) U.S. Cl. ....................... 434/185; 434/118; 434/169; 434/307 R; 704/260; 704/205
(58) Field of Search ................................ 434/116, 118, 434/156, 157, 169, 178, 185, 307 R, 308, 322, 323, 362, 365; 704/1, 205, 207, 211, 222, 270, 271, 243, 265, 503, 504; 709/203, 220, 229; 706/927; 455/12.1, 20; 324/635, 636; 340/556, 566, 572.4

(56) References Cited

U.S. PATENT DOCUMENTS

| | | | | |
|---|---|---|---|---|
| 3,816,664 A | * | 6/1974 | Koch | 704/211 |
| 4,689,553 A | * | 8/1987 | Haddox | 324/636 |
| 4,876,737 A | * | 10/1989 | Woodworth et al. | 455/12.1 |
| 5,170,432 A | * | 12/1992 | Hackbarth et al. | 704/254 |
| 5,353,011 A | * | 10/1994 | Wheeler et al. | 340/572.4 |
| 5,615,302 A | * | 3/1997 | MeEachern | 704/209 |
| 5,799,267 A | * | 8/1998 | Siegel | 704/1 |
| 5,813,862 A | | 9/1998 | Merenich et al. | |
| 5,873,061 A | * | 2/1999 | Häb-Umbach et al. | 704/254 |
| 5,957,699 A | * | 9/1999 | Peterson et al. | 434/350 |
| 6,052,512 A | * | 4/2000 | Peterson et al. | 709/220 |
| 6,071,123 A | | 6/2000 | Tallal et al. | |
| 6,076,060 A | * | 6/2000 | Lin et al. | 704/260 |
| 6,078,885 A | * | 6/2000 | Beutnagel | 704/258 |
| 6,094,633 A | * | 7/2000 | Gaved et al. | 704/260 |
| 6,123,548 A | | 9/2000 | Tallal et al. | |
| 6,210,166 B1 | | 4/2001 | Jenkins et al. | |
| 6,302,697 B1 | | 10/2001 | Tallal et al. | |

* cited by examiner

Primary Examiner—Joe H. Cheng
(74) Attorney, Agent, or Firm—James W. Huffman

(57) ABSTRACT

A method for adaptively training a human subject to process, and to distinguish between, similar acoustic events that are common in spoken language is provided. The method utilizes sequences of up/down frequency sweeps, of varying frequency and duration, and having varying inter stimulus intervals (ISI) between the frequency sweeps. A sequence is presented to the subject for order identification. The subject must listen to the up/down order of a sequence, and signal identification of the up/down order according to what s/he heard. Signal identification is provided utilizing a computer display, a mouse, and graphical buttons corresponding to the up/down frequency sweeps. Correct order identification causes the process to adaptively reduce the ISI separating the frequency sweeps, to reduce the duration of the frequency sweeps, to alter the frequency of the frequency sweeps, and to increase the number of frequency sweeps within a sequence.

13 Claims, 15 Drawing Sheets

| TRAINING STIMULUS SETS/ISI's | | | | |
|---|---|---|---|---|
| freq. (Hz) | duration (ms) | # sweeps | ISI (ms) | |
| 500 | 250 | 2 | 1000 | |
| 1000 | 250 | 2 | 1000 | |
| 2000 | 250 | 2 | 1000 | |
| | | | | |
| 500 | 200 | 2 | 1000 | |
| 1000 | 200 | 2 | 1000 | |
| 2000 | 200 | 2 | 1000 | |
| | | | | |
| 500 | 150 | 2 | 1000 | |
| 1000 | 150 | 2 | 1000 | |
| 2000 | 150 | 2 | 1000 | |
| | | | | |
| 500 | 100 | 2 | 1000 | |
| 1000 | 100 | 2 | 1000 | |
| 2000 | 100 | 2 | 1000 | |
| | | | | |
| 500 | 80 | 2 | 900 | |
| 1000 | 80 | 2 | down to | |
| 2000 | 80 | 2 | 600 | |

1540

METHOD FOR ADAPTIVELY TRAINING HUMANS TO DISCRIMINATE BETWEEN FREQUENCY SWEEPS COMMON IN SPOKEN LANGUAGE

This application is a Divisional of prior U.S. patent application Ser. No. 09/098,199, filed Jun. 16, 1998, entitled "METHOD FOR ADAPTIVELY TRAINING HUMANS TO DISCRIMINATE BETWEEN FREQUENCY SWEEPS COMMON SPOKEN LANGUAGE", now U.S. Pat. No. 6,210,166, which is a Continuation-in-Part of U.S. patent application Ser. No. 08/982,189, filed Dec. 17, 1997, entitled "METHOD FOR APPARATUS FOR TRAINING OF SENSORY AND PERCEPTUAL SYSTEMS IN LLI SUBJECT", now U.S. Pat. No. 5,927,988; and is related to U.S. patent application Ser. No. 08/992,071, filed Dec. 17, 1997, entitled "METHOD AND APPARATUS FOR TRAINING OF SENSORY AND PERCEPTUAL SYSTEMS IN LLI SUBJECTS", now U.S. Pat. No. 6,019,607; U.S. patent application Ser. No. 08/992,072, filed Dec. 17, 1997, entitled "METHOD AND APPARATUS FOR TRAINING OF COGNITIVE AND MEMORY SYSTEMS IN HUMANS", now U.S. Pat. No. 6,159,014; and U.S. patent application Ser. No. 09/089,149, filed Jun. 2, 1998, entitled "METHOD AND APPARATUS FOR TRAINING OF AUDITORY/VISUAL DISCRIMINATION USING TARGET AND DISTRACTOR PHONEMES/ GRAPHEMES", now U.S. Pat. No. 6,190,173, all of which are assigned to Scientific Learning Corporation.

BACKGROUND OF THE INVENTION

1. Field of the Invention

This invention relates in general to the field of language education, and more specifically to a computer program for training a human's auditory processing system to discriminate between and accurately identify frequency sweeps that are common in spoken language.

2. Description of the Related Art

Up to ten percent of children have language-learning impairments (LLI) resulting from the inability to accurately process short duration acoustic events at the rates that occur in normal speech. Their trouble distinguishing among elements of speech is neurologically based and has far reaching consequences, including: academic failure, emotional and disciplinary problems, and possibly diminished lifelong achievement and self-image. No bracket of intelligence, race, gender or economic level is immune from this problem.

More specifically, children with LLI have difficulty detecting and identifying sounds that occur simultaneously or in close proximity to each other—a phenomenon known as "masking." Because of masking, children with LLI require sounds that are as much as 45 decibels more intense than a preceding or subsequent masking noise to distinguish and understand them. In addition, children with LLI are consistently poorer at detecting a brief tone presented with a masking noise, particularly when the brief tone is turned on immediately prior to the masking noise. This phenomenon is called "backward masking." Similarly, when the brief tone is turned on immediately after the masking noise a similar decrease in detectability can occur. This phenomenon is called "forward masking". For a tone to be detected by a child with LLI in the presence of a masking noise, the tone must be separated in time or frequency from the masking noise.

The inability to accurately distinguish and process short duration sounds often causes children to fall behind in school. Since the children can't accurately interpret many language sounds, they can't remember which symbols represent which sounds. This deficiency causes difficulties in learning to read (translating from symbols to sounds), and in spelling. In fact, it is common for a child with LLI to fall two to three years behind his/her peers in speech, language and reading development.

One way children develop such auditory processing problems is from middle ear infections when they are young and beginning to develop the oral representations of language in the central auditory nervous system. When a child has an ear infection, fluid can build up and block or muffle the sound wave entering the ear causing intermittent hearing loss. Even if the infection doesn't permanently damage the ear, the child's brain doesn't learn to process some sounds because it hasn't heard them accurately before, on a consistent basis. This typically occurs during a critical period of brain development when the brain is building the nerve connections necessary to accurately process acoustic events associated with normal speech.

Researchers believe that the auditory processing problem is essentially one of timing. Vowel sounds like /a/ and /e/ usually last at least 100 milliseconds and typically have constant frequency content. Consonants, on the other hand, typically have modulated frequency components, and last less than 40 milliseconds. Children with LLI cannot process these faster speech elements, especially the hard consonants like /t/, /p/, /d/ and /b/, if they occur either immediately before or after vowels, or if they are located near other consonants. Rather than hearing the individual sounds that make up a particular phoneme, children with LLI integrate closely associated sounds together over time. Since the duration of vowels are typically longer than consonants, the modulated frequency portions of consonants are often lost in the integration, an affect that may also hinder the resolution of the vowel, particularly short duration vowels.

This problem of abnormal temporal integration of acoustic events over time is not limited to children with LLI. Rather, the problem extends to stroke victims who have lost the neurological connections necessary to process speech, as well as to individuals raised in one country, having one set of language phonemes, and attempting to learn the language of another country, having a distinct set of language phonemes. For example, it is known that an individual raised in Japan is not often presented with phonemes similar to the English r's and l's, because those consonants are not common in the Japanese language. Similarly, there are many subtleties in the sounds made by a speaker of Japanese that are difficult to distinguish unless raised in Japan. The phonetic differences between languages are distinctions that must be learned, and are often very difficult. But, they are clearly problems that relate to the temporal processing of short duration acoustic events.

The above described temporal processing deficiency has little if anything to do with intelligence. In fact, some LLI specialists argue that brains choosing this different route by which to absorb and reassemble bits of speech may actually stimulate creative intelligence, but at the expense of speech and reading problems.

Recent studies have shown that if the acoustic events aassociated with phonemes that are difficult to distinguish, such as /ba/ and /da/, are slowed down, or that the consonant portion of the phonemes are emphasized, that students diagnosed as LLI can accurately distinguish between the phonemes. In addition, if the interval between two complex sounds is lengthened, LLI students are better able to process the sounds distinctly.

Heretofore, the solution to the processing problem has been to place LLI students in extended special education and/or speech therapy training programs that focus on speech recognition and speech production. Or, more commonly, repetitive reading programs, phonic games, or other phonic programs are undertaken. These programs often last for years, with a success rate that is often more closely associated with the skill of the speech and language professional than with the program of study.

What is needed is a method and apparatus that allows a subject with abnormal temporal processing to train, or retrain their brain to recognize and distinguish short duration acoustic events that are common in speech. Moreover, what is needed is a program that repetitively trains a subject to distinguish between frequency sweeps that are common in spoken language, by first stretching the frequency sweeps in time, and by separating them to the point that they are distinguishable, and then adaptively adjusting the stretching and separation of the frequency sweeps to the level of normal speech. The adaptive adjustments should be made so as to encourage the subject to continue with the repetitions, and the number of repetitions should be sufficient to develop the necessary neurological connections for normal temporal processing of speech. Moreover, the program should provide acoustic signals to the brain that are better for phonetic training than normal human speech.

SUMMARY

To address the above-detailed deficiencies, the present invention provides a method for adaptively developing neural activity, to improve signal differentiation in spoken language, the method presenting sequences of frequency sweeps of varying duration, separated by an inter stimulus interval (ISI) of varying length, and with a varying number of frequency sweeps in each sequence. The method adaptively trains a subject to distinguish between auditorily presented frequency sweeps that are common in spoken language. The method includes: presenting a sequence of at least two frequency sweeps to a subject, the frequency sweeps separated by a predetermined inter stimulus interval (ISI); requiring the subject to signal identification of the frequency sweeps, in the order in which they are presented; and adaptively reducing or increasing the ISI separating the frequency sweeps as the subject incorrectly or correctly identifies their order of presentation, respectively.

In another aspect, the method trains a subject to process and distinguish upward and downward going frequency sweeps of frequency f, separated by a predetermined inter stimulus interval (ISI). The method includes: presenting a sequence containing a plurality of frequency sweeps to a subject for order identification, where the sequence has at least one upward going sweep and at least one downward going sweep; requiring the subject to signal identification of the order of the plurality of frequency sweeps presented in the sequence; and after the subject correctly identifies the order of the plurality of frequency sweeps in a plurality of presented sequences, increasing the number of frequency sweeps in the sequence.

In yet another aspect, the present invention describes a method for training a subject to discriminate between acoustic events that are common in spoken language by using sequences of upward and downward going frequency sweeps of frequency f, and duration d, and separated by an inter stimulus interval (ISI), the frequency sweeps presented to the subject for order identification. The method includes: presenting a sequence having a plurality of upward and downward going frequency sweeps to the subject for order identification; providing buttons associated with the upward and downward going frequency sweeps to allow the subject to signal order identification for the presented sequence; recording whether the subject's signaled identification corresponds to the presented sequence (i.e., correct or incorrect); repeating a)–c); after a predetermined number of correct identifications, reducing the ISI; after a predetermined number of correct identifications, reducing d; and after a predetermined number of correct identifications, increasing the number of frequency sweeps presented in a sequence.

BRIEF DESCRIPTION OF THE DRAWINGS

These and other objects, features, and advantages of the present invention will become better understood with regard to the following description, and accompanying drawings where.

DETAILED DESCRIPTION

Figure 1:
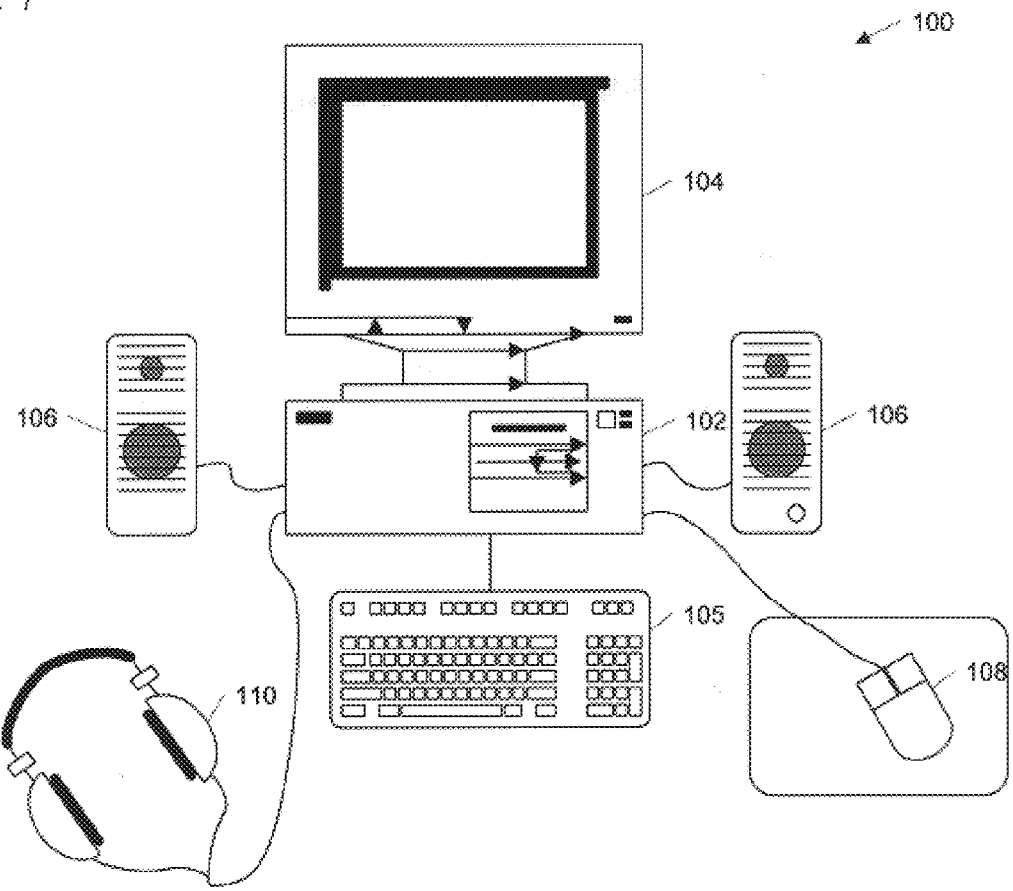
FIG. 1 is a block diagram of a computer system for executing a program according to the present invention.

Referring to FIG. 1, a computer system 100 is shown for executing a computer program to train, or retrain a subject, according to the present invention. The computer system 100 contains a computer 102, having a CPU, memory, hard disk and CD ROM drive (not shown), attached to a monitor 104. The monitor 104 provides visual prompting and feedback to the subject during execution of the computer program. Attached to the computer 102 are a keyboard 105, speakers 106, a mouse 108, and headphones 110. The speakers 106 and the headphones 110 provide auditory prompting and feedback to the subject during execution of the computer program. The mouse 108 allows the subject to navigate through the computer program, and to select particular responses after visual or auditory prompting by the computer program. The keyboard 105 allows an instructor to enter alpha numeric information about the subject into the computer 102. Although a number of different computer platforms are applicable to the present invention, embodiments of the present invention execute on either IBM compatible computers or Macintosh computers.

Figure 2:
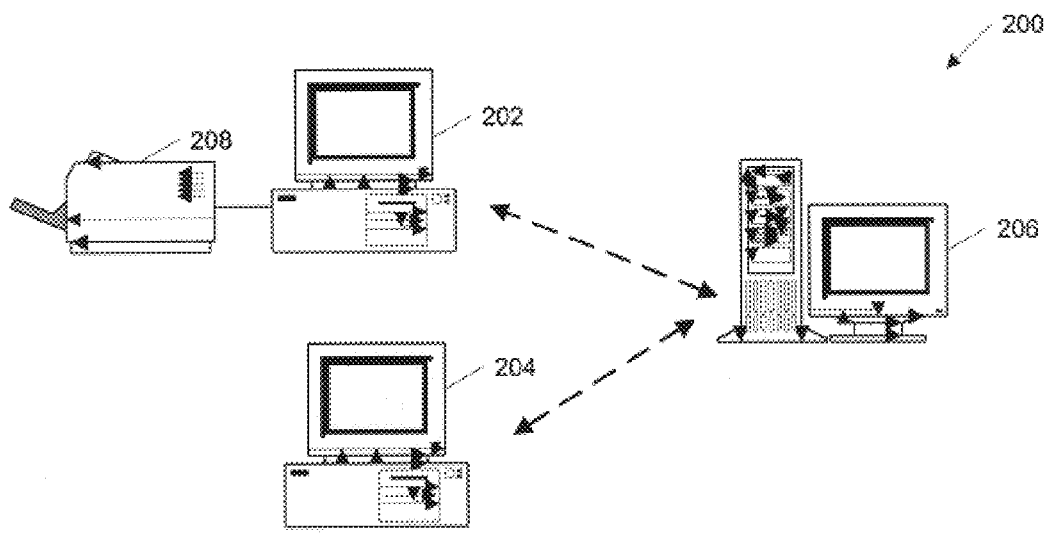
FIG. 2 is a block diagram of a computer network for executing a program according to the present invention.

Now referring to FIG. 2, a computer network 200 is shown. The computer network 200 contains computers 202, 204, similar to that described above with reference to FIG. 1, connected to a server 206. The connection between the computers 202, 204 and the server 206 can be made via a local area network (LAN), a wide area network (WAN), or via modem connections, directly or through the Internet. A printer 208 is shown connected to the computer 202 to illustrate that a subject can print out reports associated with the computer program of the present invention. The computer network 200 allows information such as test scores, game statistics, and other subject information to flow from a subject's computer 202, 204 to a server 206. An administrator can then review the information and can then download configuration and control information pertaining to a particular subject, back to the subject's computer 202, 204.

Before providing a detailed description of the present invention, a brief overview of certain components of speech will be provided, along with an explanation of how these components are processed by LLI subjects. Following the overview, general information on speech processing will be provided so that the reader will better appreciate the novel aspects of the present invention.

Figure 3:
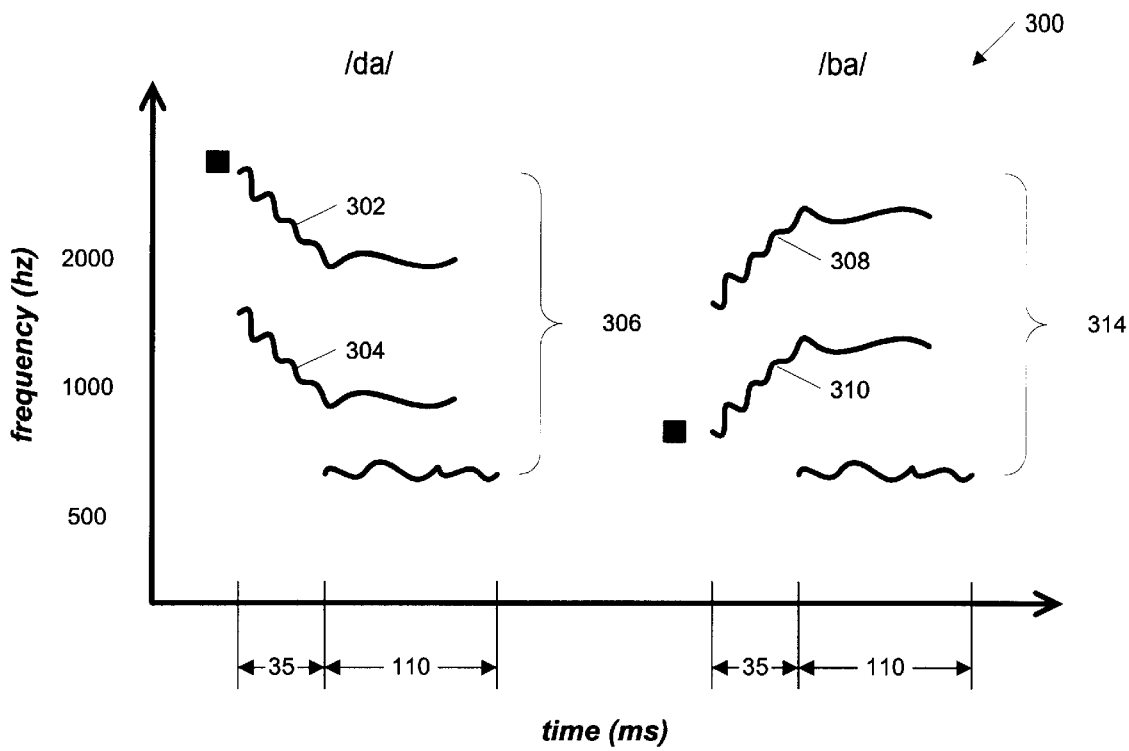
FIG. 3 is a chart illustrating frequency/energy characteristics of two phonemes within the English language.

Referring to FIG. 3, a chart is shown that illustrates frequency components, over time, for two distinct phonemes within the English language. Although different phoneme combinations are applicable to illustrate features of the present invention, the phonemes /da/ and /ba/ are shown. For the phoneme /da/, a downward sweep frequency component 302, at approximately 2.5–2 khz is shown to occur over a 35 ms interval. In addition, a downward sweep frequency component 304, at approximately 1 khz, is shown to occur during the same 35 ms interval. At the end of the 35 ms interval, constant frequency components 306 are shown, whose duration is approximately 110 ms. Thus, in producing the phoneme /da/, the stop consonant portion of the element /d/ is generated, having high frequency sweeps of short duration, followed by a long vowel element /a/ of constant frequency.

Also shown are frequency components for a phoneme /ba/. This phoneme contains an upward sweep frequency component 308, at approximately 2 khz, having a duration of approximately 35 ms. The phoneme also contains an upward sweep frequency component 310, at approximately 1 khz, during the same 35 ms period. Following the stop consonant portion /b/ of the phoneme, are constant frequency vowel portions 314 whose duration is approximately 110 ms.

Thus, both the /ba/ and /da/ phonemes begin with stop consonants having modulated frequency components of relatively short duration, followed by a constant frequency vowel components of longer duration. The distinction between the phonemes exists primarily in the 2 khz sweeps during the initial 35 ms interval. Similarity exists between other stop consonants such as /ta/, /pa/, /ka/ and /ga/.

Figure 4:
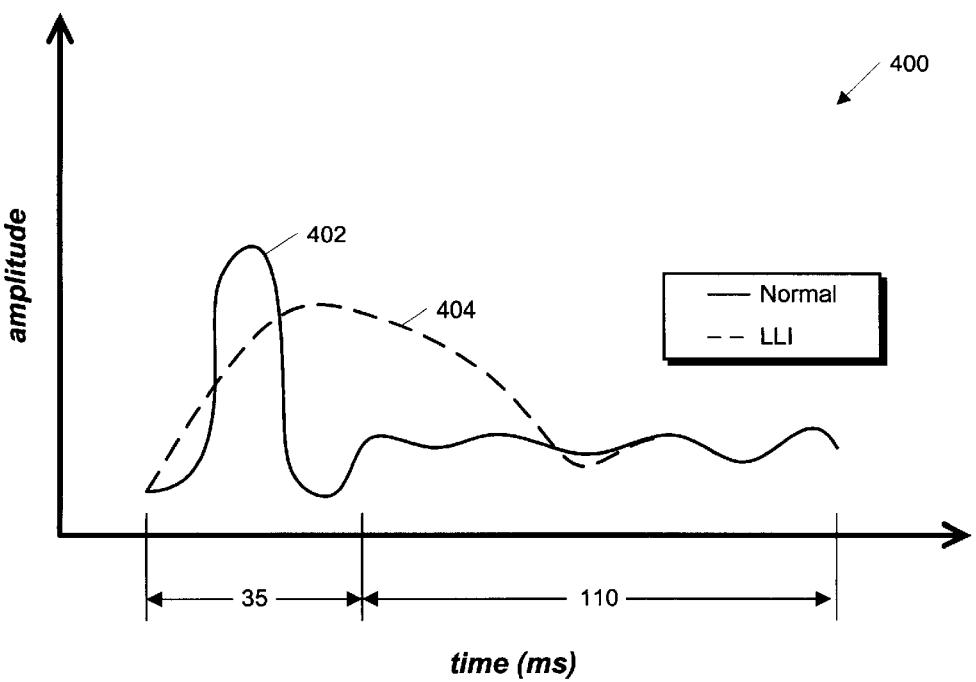
FIG. 4 is a chart illustrating auditory reception of a phoneme by a subject having normal receptive characteristics, and by a subject whose receptive processing is impaired.

Referring now to FIG. 4, the amplitude of a phoneme, for example /ba/, is viewed in the time domain. A short duration high amplitude peak waveform 402 is created upon release of either the lips or the tongue when speaking the consonant portion of the phoneme, that rapidly declines to a constant amplitude signal of longer duration. For an individual with normal temporal processing, the waveform 402 will be understood and processed essentially as it is. However, for an individual who is learning-language impaired, or who has abnormal temporal processing, the short duration, higher frequency consonant burst will be integrated over time with the lower frequency vowel, and depending on the degree of impairment, will be heard as the waveform 404. The result is that the information contained in the higher frequency sweeps associated with consonant differences, will be muddled, or indistinguishable.

With the above general background of speech elements, and how LLI subjects process them, a general overview of speech processing will now be provided. As mentioned above, one problem that exists in LLI subjects is the inability to distinguish between short duration acoustic events. If the duration of these acoustic events is stretched, in the time domain, it is possible to train LLI subjects to distinguish between these acoustic events. An example of such time domain stretching is shown in FIG. 5, to which attention is now directed.

Figure 5:
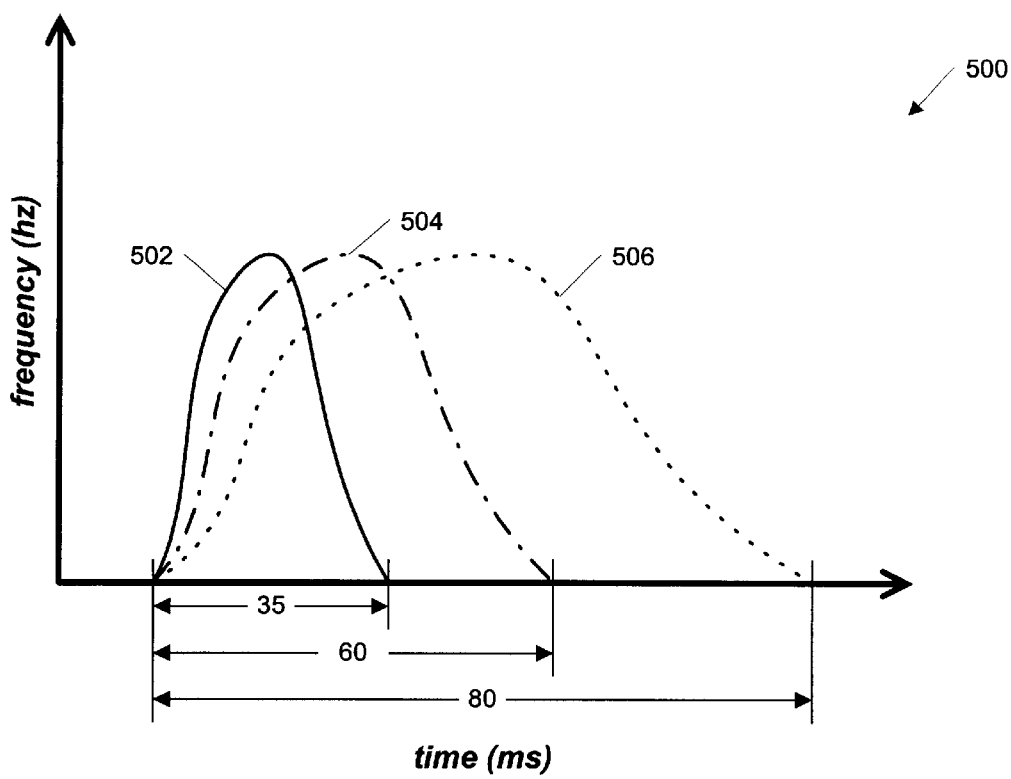
FIG. 5 is a chart illustrating stretching of a frequency envelope in time, according to the present invention.

In FIG. 5, a frequency vs. time graph 500 is shown that illustrates a waveform 502 having short duration characteristics similar to the waveform 402 described above. Using existing computer technology, the analog waveform 502 can be sampled and converted into digital values. The values can then be manipulated so as to stretch the waveform in the time domain to a predetermined length, while preserving the amplitude and frequency components of the modified waveform. The modified waveform can then be converted back into an analog waveform for reproduction by a computer, or by some other audio device. The waveform 502 is shown stretched in the time domain to durations of 60 ms (waveform 504), and 80 ms (waveform 506). By stretching the consonant portion of the waveform 502 without effecting its frequency components, subjects with LLI can begin to hear distinctions in common phonemes.

Figure 6:
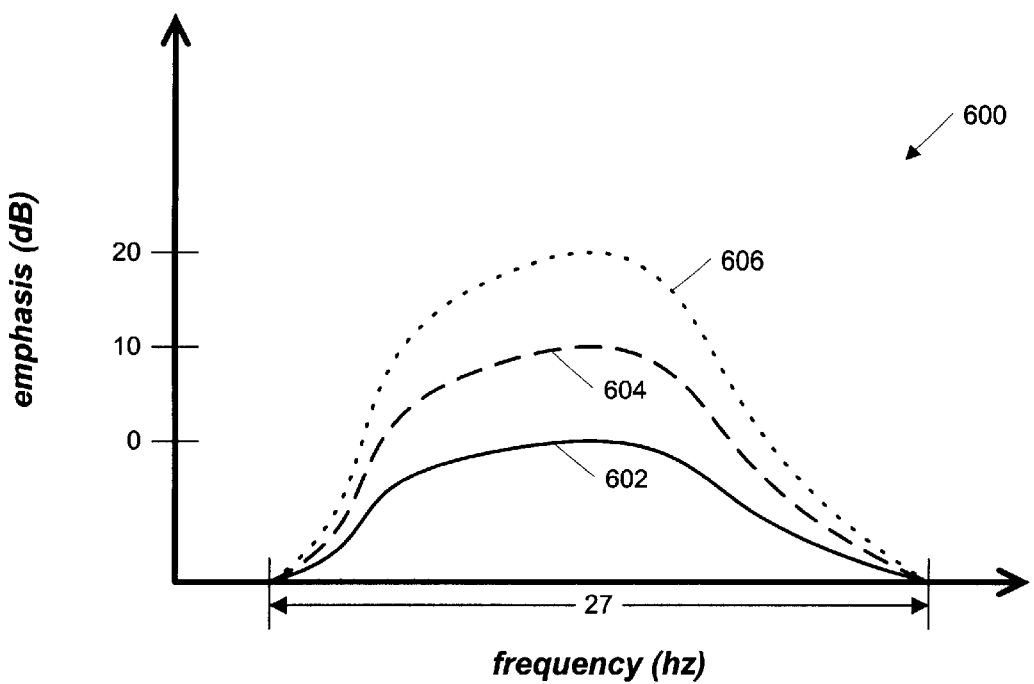
FIG. 6 is a chart illustrating emphasis of selected frequency components, according to the present invention.

Another method that may be used to help LLI subjects distinguish between phonemes is to emphasize selected frequency envelopes within a phoneme. Referring to FIG. 6, a graph 600 is shown illustrating a frequency envelope 602 whose envelope varies by approximately 27 hz. By detecting frequency modulated envelopes that vary from say 3–30 hz, similar to frequency variations in the consonant portion of phonemes, and selectively emphasizing those envelopes, they are made more easily detectable by LLI subjects. A 10 dB emphasis of the envelope 602 is shown in waveform 604, and a 20 dB emphasis in the waveform 606.

Figure 7:
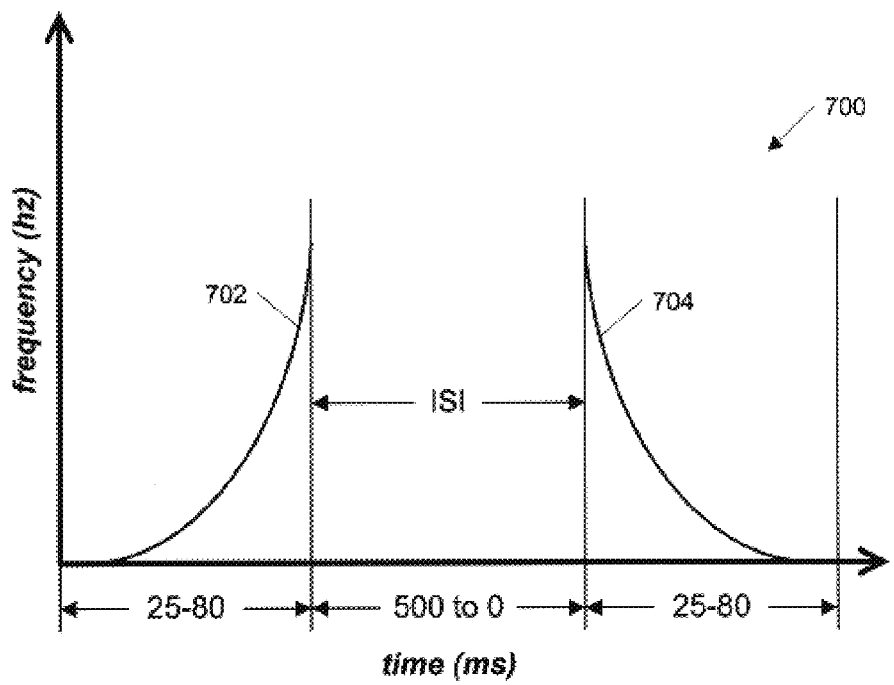
FIG. 7 is a chart illustrating up-down frequency sweeps of varying duration, separated by a selectable inter-stimulus-interval (ISI), according to the present invention.

A third method that may be used to train LLI subjects to distinguish short duration acoustic events is to provide frequency sweeps of varying duration, separated by a predetermined interval, as shown in FIG. 7. More specifically, an upward frequency sweep 702, and a downward frequency sweep 704 are shown, having duration's varying between 25 and 80 milliseconds, and separated by an inter-stimulus interval (ISI) of between 500 and 0 milliseconds. The duration and frequency of the sweeps, and the inter-stimulus interval between the sweeps are varied depending on the processing level of the LLI subject, as will be further described below.

Utilization of up-down frequency sweeps with varying ISI has been fully described in U.S. Patent application No. 5,813,862, entitled "METHOD AND DEVICE FOR ENHANCING THE RECOGNITION OF SPEECH AMONG SPEECH-IMPAIRED INDIVIDUALS", and is hereby incorporated by reference.

The above described methods have been combined in a unique fashion by the present invention to provide an adaptive training method and apparatus for training subjects having abnormal temporal processing abilities to recognize and distinguish short duration acoustic events that are common in speech. More specifically, emphasis has been used to intensify format transitions of stop consonants that are presented to a subject. It is believed that the differential gain of critical acoustic components generates more vigorous neural activity, which leads to better signal differentiation by neural networks involved in speech perception.

The present invention is embodied into a computer program entitled Fast ForWord II by Scientific Learning Corporation. The computer program is provided to an LLI subject via a CD-ROM that is input into a general purpose computer such as that described above with reference to FIG. 1. In addition, a subject may log onto a server, via an Internet connection, for example, to upload test results, and to download training parameters for future exercises. Specifics of the present invention will now be described with reference to FIGS. 8–16.

Figure 8:
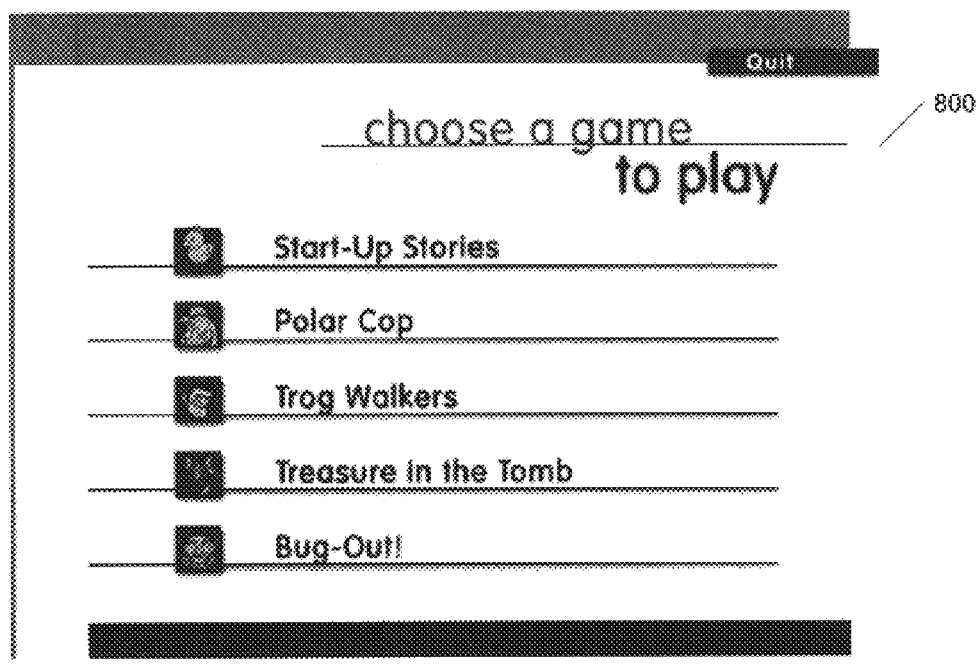
FIG. 8 is a pictorial representation of a game selection screen according to the present invention.

Referring first to FIG. 8, a pictorial representation is shown of a game selection screen 800. The game selection screen 800 is similar to that provided to a subject upon initialization of the computer program according to the present invention. The game selection screen 800 includes the titles of five computer games that provide distinct training exercises for improving language recognition in subjects who abnormally process temporal acoustic events, and for building, or rebuilding the neurological connections necessary to accurately process phonemes at the rates common in speech. The game titles include: 1) Start-Up Stories; 2) Polar Cop; 3) Trog Walkers; 4) Treasure in the Tomb; and 5) Bug-Out!.

When a subject begins execution of the Fast ForWord II computer program, s/he is presented with a screen similar to the screen 800. More specifically, upon initiation of the program, the subject is presented with a screen that lists the subjects that are currently being trained by the program. The subject, or instructor, then selects his/her name from the list. Once the subject has selected his/her name, a screen similar to 800 appears, typically listing the five programs, according to a training schedule that is dictated by the program, or is modified by an instructor. The order of the games that is presented in the screen 800 may vary from day to day, depending on which games the subject has previously played. In addition, after a subject has completed play of a particular game, that game may be shown "grayed out", indicating that it may not be selected again that day unless all other scheduled exercises have already been played. The subject then selects to play one of the games listed.

In one embodiment, a training schedule is provided by a certified Speech and Language Professional (SLP), and the SLP oversees each training session according to the schedule. An exemplary schedule requires a subject to cycle through the games for an hour and forty minutes, five days per week, for approximately six weeks.

In an alternative embodiment, the game schedule is specified by an SLP at a remote server, and the daily parameters of the schedule are downloaded to the subject's computer, either daily or weekly. The schedule can be optimized over the course of the training program according to the performance or skill of the subject. It can also be used to help manage time in each game so that all of the games are completed in about the same time at the end of the training program. This can be accomplished by an automated computer algorithm that adjusts the time allotted for each training exercise. This algorithm is individually adaptive and can adjust the times for each exercise on an individual subject basis using performance and estimates of time to complete the entire training sequence. This embodiment allows a subject to obtain the benefits of the Fast ForWord II program, and the oversight of a certified SLP, regardless of his/her geographic location. One skilled in the art will appreciate that the training schedule could either be provided in a window on the subject's computer, or could actually control the game selection screen to prompt the subject only for those games required on a particular day.

Once a subject selects a particular game, s/he is taken into that particular game's module. Alternatively, once the subject selects his/her name from the list, the particular games may be presented, in a predefined order, without requiring the subject to first select the game.

The present application provides a detailed description of the game entitled "Trog Walkers". The other games shown in FIG. 8 are described in co-pending U.S. patent applications: SLC:810 (Polar Cop); SLC:812 (Treasure in the Tomb); SLC:813 (Bug Out!); and SLC:814 (Start-Up Stories), which are hereby incorporated by reference.

Trog Walkers is a game that adaptively trains a subject to distinguish between upward and downward frequency sweeps that are common in the stop consonant portion of phonemes, by varying the duration and frequency of the sweeps, and by varying the inter-stimulus interval (ISI) between presentation of the sweeps. More specifically, the game presents a series of trials that provide sequences of upward/downward going frequency sweeps to the subject for identification. As the subject accurately identifies the upward/downward frequency sweeps, the ISI separating the sweeps is reduced, and the duration of the sweeps is reduced, ultimately to the level of normal speech. The trials are placed within a game environment to entertain and amuse the subject so that multiple iterations are considered enjoyable rather than tedious.

The premise of the Trog Walkers game is that of a running race, with the subject represented by a running character that stays a little left of mid screen as the landscape rolls by. The player races against 8 other runners, whose speed varies. Correct responses to trials cause the running character to speed up, while incorrect responses cause the running character to slow down.

A complete description of the trial methodology used by Trog Walkers, as well as the frequencies tested, and the adaptive nature of the game, will be provided below with reference to FIGS. 15–16. However, to better appreciate the methodology used within Trog Walkers, an overview of the game will first be provided, with reference to several screens within the game.

Figure 9:
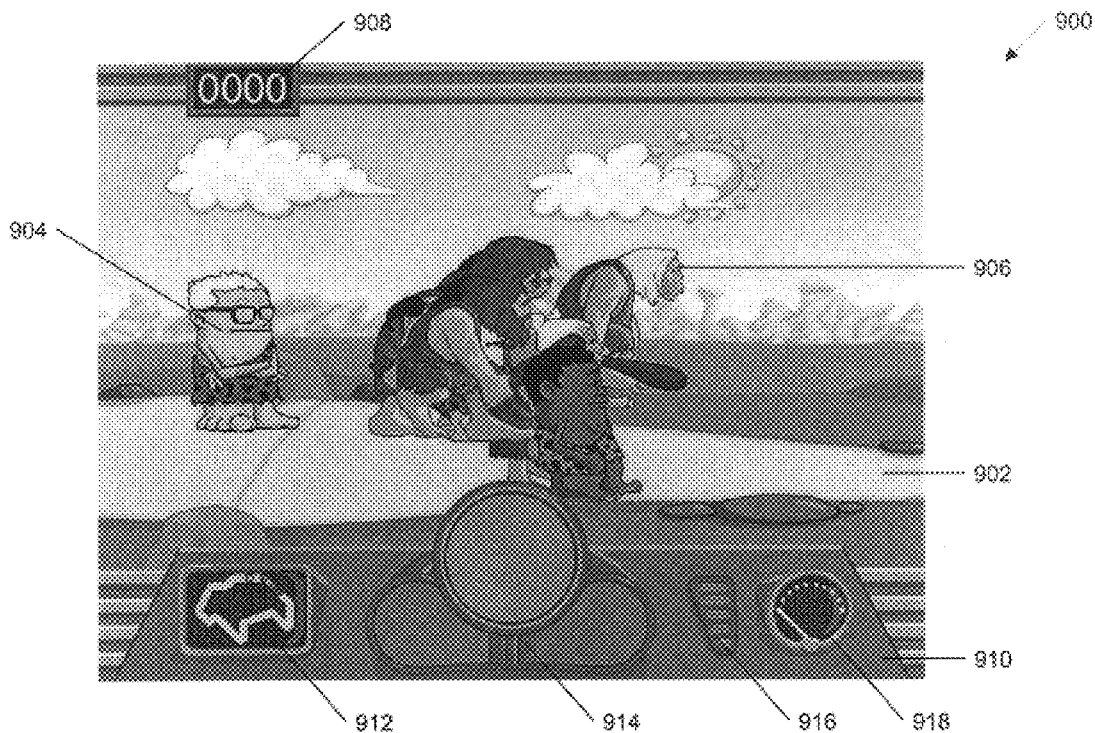
FIG. 9 is a pictorial representation of an initial game screen for a game entitled "Trog Walkers" according to the present invention.

Referring to FIG. 9, a screen 900 is shown that contains a view of a racetrack 902, a character runner 904 (representing the subject), a group of competing runners 906, a scoreboard 908, and a dashboard 910. The dashboard 910 provides the subject with an indication of his/her status or progress in the game.

More specifically, the dashboard 910 includes a map 912 of the racetrack, with individual highlighted indicators illustrating the position of the character runner 904, and the competing runners 906 on the track 902. The dashboard 910 also includes a gear shift indicator 916 that contains 5 highlighted areas. When playing the game, the number of areas highlighted indicates how many frequency sweeps will be presented to the subject in the next trial. In one embodiment of the present invention, from 2 to 5 frequency sweeps are presented in each trial for identification. The dashboard 910 further includes a speedometer 918 for indicating how fast the character runner 904 is running. In one embodiment, the speed of the character runner 904 is based on the number of correct responses provided by the subject in the previous 10 trials. The character runner 904 begins at speed level 1, and as correct responses are provided, his speed increases up to a maximum speed level of 10. A control panel 914 is also included on the dashboard 910. The control panel 914 provides an area for the subject to initiate trials, and provide responses, as will now be described with reference to FIG. 10.

Figure 10:
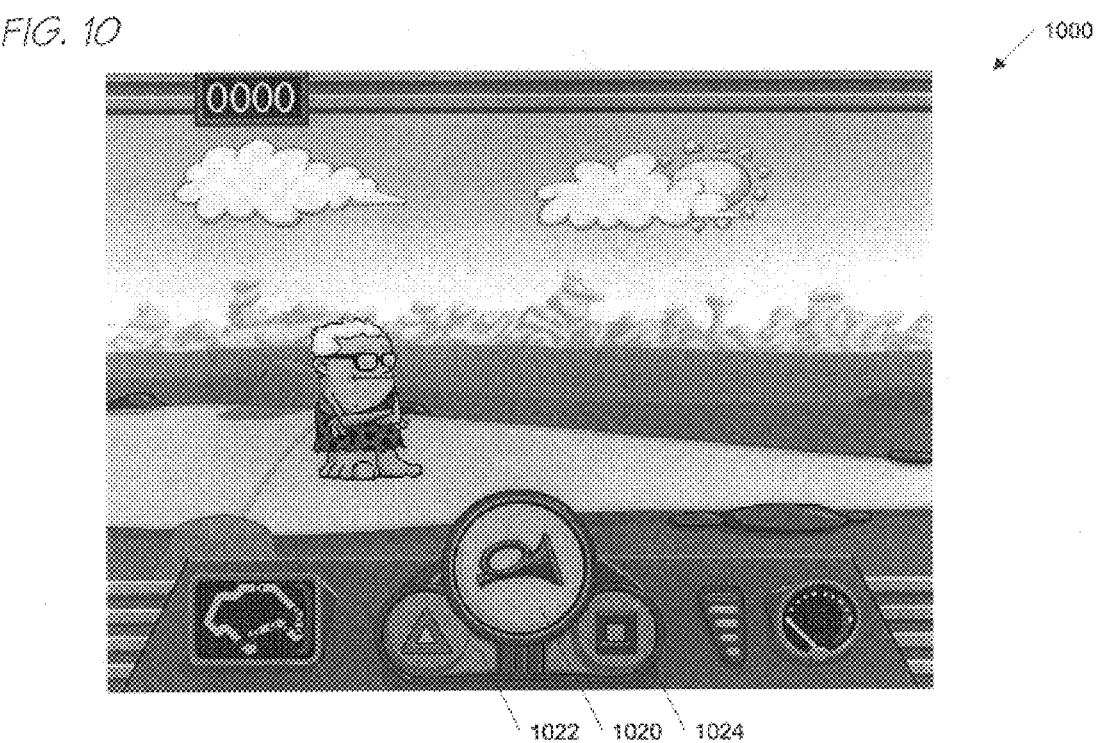
FIG. 10 is a pictorial representation of a game screen in Trog Walkers illustrating initiation of a sweep sequence trial.

In FIG. 10, a screen 1000 is shown that includes all of the elements listed in FIG. 9. In addition, a control panel is shown that includes a trial initiation button 1020, and two response buttons 1022, 1024. The subject initiates a trial by placing a cursor over the trial initiation button 1020 and pressing a button on a computer mouse, such as the one described above with reference to FIG. 1. When the button 1020 is depressed, a trial is begun. A trial consists of a sequence of at least 2 frequency sweeps being presented to the subject. The frequency sweeps may be presented by playing the frequency sweeps through a computer, either via speakers or headphones, such as those shown in FIG. 1.

The frequency sweeps may either be upward or downward. That is, given a starting frequency, each of the frequency sweeps will either increase in frequency, or decrease in frequency. In addition, each of the frequency sweeps in a sequence are separated from each other by a predetermined amount of time. After the sequence is played for the subject, the subject must then identify the order of the frequency sweeps by pressing a corresponding response button 1022, 1024. In one embodiment, the button 1022 corresponds to an upward going sweep, and the button 1024 corresponds to a downward going sweep. Thus, if the sequence played for the subject is up/down, the subject correctly identifies the sequence by first pressing button 1022, and then pressing 1024. Any other button combination is considered an incorrect response. A correct identification causes the running character to increase in speed, and gain on the competing runners. An incorrect identification causes the running character to decrease in speed, and fall behind the competing runners.

Figure 11:
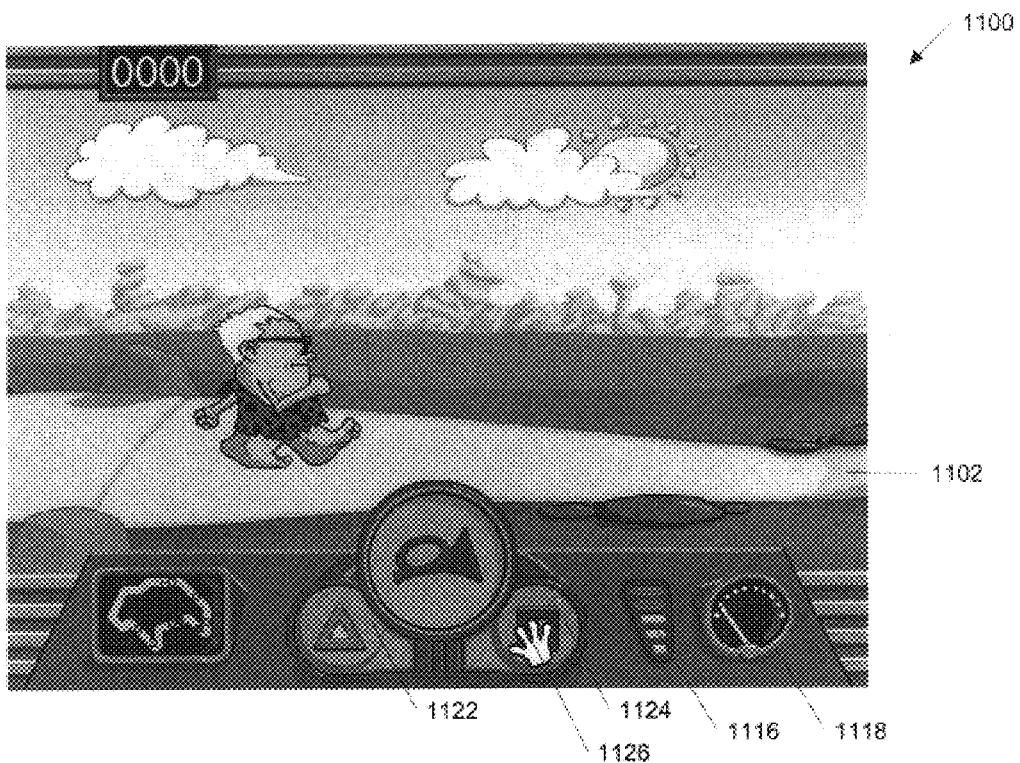
FIG. 11 is a pictorial representation of a game screen in Trog Walkers illustrating selection of frequency sweep order in a trial.

Referring now to FIG. 11, a screen 1100 is shown. The screen 1100 includes all of the elements described above in FIGS. 9–10, with the hundreds digits replaced by 11. FIG. 11 however, particularly illustrates selection of the button 1124 by a hand cursor 1126. That is, to correctly identify a sequence of frequency sweeps, the subject moves the hand cursor 1126 on top of either the button 1124, or the button 1126, as appropriate, and selects the button by pressing down on the mouse key.

Also shown in FIG. 11 is the character runner 1104, illustrating his running on the racetrack 1102. The speed of the character runner 1104 is at level 2, as shown by the speedometer 1118. In addition, the shift indicator 1116 is shown with 3 of the 5 areas highlighted, indicating that the subject is being tested on sequences that include 3 frequency sweeps.

Figure 12:
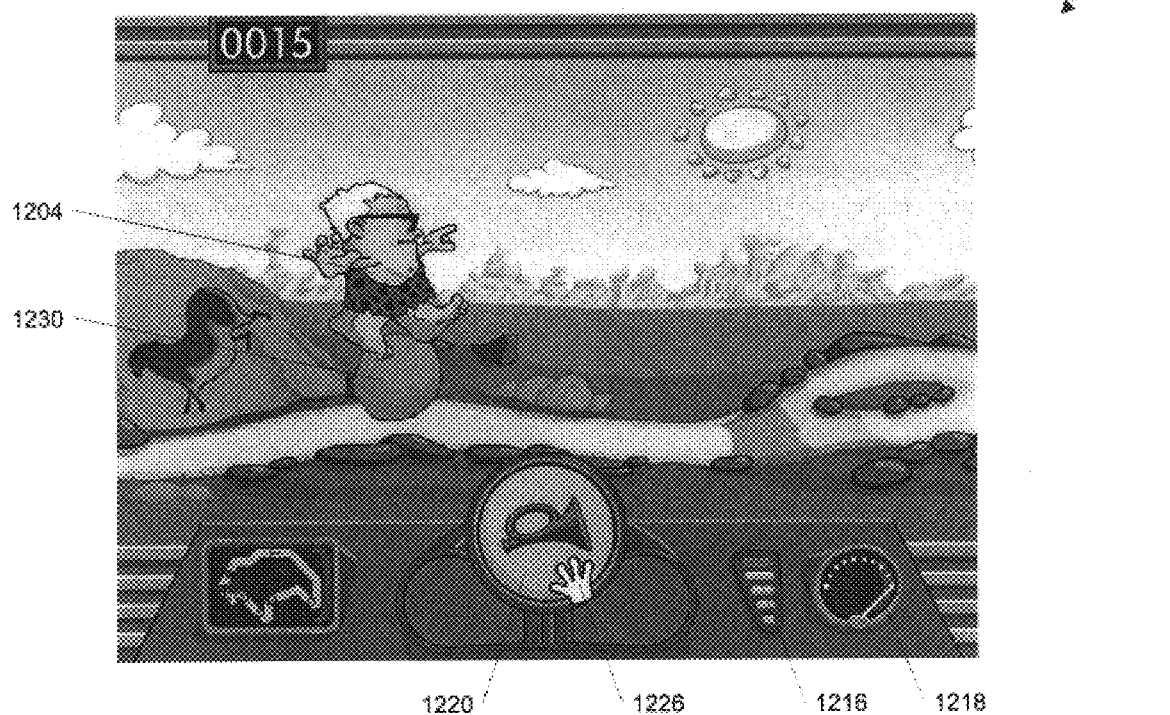
FIG. 12 is a pictorial representation of a game screen in Trog Walkers illustrating a reward animation for correctly responding to a number of sequential trials.

Referring now to FIG. 12, a screen 1200 is shown. The screen 1200 shows all of the elements described above, with the hundreds digit replaced by 12. Particularly, the screen 1200 shows the shift indicator 1216 with 4 highlighted areas, indicating that 4 frequency sweeps will be presented to the subject for identification, a running speed level of 10, as shown by the speedometer 1218, and the running character 1204 on top of a boulder 1230. The boulder 1230 is one of a number of visual awards that are provided to the subject, as s/he progresses through the game, to add further interest in game play. A hand cursor 1226 is shown on top of the trial initiation button 1220. As mentioned above, when the subject depresses the button 1220, another sequence of frequency sweeps is presented for identification.

Figure 13:
FIG. 13 is a pictorial representation of a game screen in Trog Walkers illustrating the subject's character overtaking competitors in the race.

Referring now to FIG. 13, a screen 1300 is shown. The screen 1300 shows all of the elements described above, with the hundreds digit replaced by 13. Particularly, the screen 1300 illustrates the character runner 1304 catching the competing runners 1306. In one embodiment, the competing runners 1306 take off from the start line, leaving the character runner 1304 behind. They then evenly distribute themselves on the racetrack. As the subject correctly responds to a number of trials, the character runner 1304 passes them as a function of the correctness of his/her responses.

Figure 14:
FIG. 14 is a pictorial representation of a game screen in Trog Walkers illustrating the emcee of the race waving a finishing flag.

Referring now to FIG. 14, a screen 1400 is shown. The screen 1400 shows all of the elements described above, with the hundreds digit replaced by 14. Particularly, the screen 1400 illustrates a game emcee 1440. The game emcee 1440 introduces the story line and the interface the first time a subject enters the game. The emcee 1440 starts each race by waving a flag. If the subject completes a race, the emcee 1440 waves a checkered flag as the character runner 1404 crosses the finish line. If the subject ends a day of play in the middle of a race, the emcee 1440 announces a halt to the race, and then when the subject next plays, the emcee 1440 announces resumption of the race from that point. In addition, the emcee 1440 announces when the number of elements in the current stimulus set (to be further described below) has changed.

With the above overview of the Trog Walkers game, a detailed description of the methodology, and adaptive controls of the game will now be provided.

FREQUENCY SWEEP SEQUENCES

In one embodiment, Trog Walkers provides trials to train a subject to distinguish between upward and downward frequency sweeps, using different frequencies, different frequency durations, different spacings between frequency sweeps, and a differing number of frequency sweeps within each trial sequence. Specifics of each of these elements will now be provided.

SWEEP FREQUENCY

Trog Walkers trains a subject to distinguish between upward and downward going frequency sweeps using three different starting frequencies: 500, 1000 and 2000 hertz. FM sweeps are created for each of these starting frequencies that sweep up/down at a rate of approximately 16 octaves per second, a rate that is common in spoken language. However, during an initial training portion of the game, when frequency sweeps are extended to allow for maximum detection (200–250 ms duration), the sweep rates are slightly reduced for the 1000 and 2000 Hz sweeps to insure correct playback by the computer throughout the duration of each sweep. Such sweep rate modification is provided to prevent long sweeps starting at higher frequencies from ending in distortion.

SWEEP DURATION

The duration of each of the frequency sweeps, at each frequency are also varied to provide trials of increasing difficulty for a subject. Initially, frequency sweeps are provided with a duration of 250 ms. As the subjects skill level improves, the sweep duration is reduced, first to 200 ms, then to 100 ms, then to 80 ms, and finally to 30 ms.

OF SWEEPS IN A SEQUENCE

The game begins by presenting two frequency sweeps in each sequence to the subject for identification. The possible combinations of frequency sweeps therefore contains: up/up, up/down, down/up and down/down. As the subject correctly distinguishes between the frequency sweeps, at a given sweep frequency and duration, the number of frequency sweeps within a sequence increases linearly (as will be further described below) to a maximum of five. For example, if four frequency sweeps per sequence is being presented to a subject, there would be sixteen possible combinations of up/down constructs.

To decrease the number of possible patterns, and to maximize the cognitive load for the subject, an approximately even number of up/down sweeps in a sequence is maintained. That is, simple non-memory-requiring tasks such as up/up/up/up/up are eliminated. In one embodiment, Trog Walkers uses the following criteria to develop sequences.

| # of frequency sweeps presented | Maximum # of upward sweeps |
| --- | --- |
| 2 | 1 |
| 3 | 1 or 2 |
| 4 | 2 |
| 5 | 2 or 3 |

STIMULUS SETS

A stimulus set defines the frequency for a sequence of frequency sweeps, the duration of the frequency sweeps, and the number of frequency sweeps presented in a sequence. Thus, in the following discussion, shorthand notation for a stimulus set will be represented in the form [frequency_stimulus duration_# of sweeps]. For example, [500_250_2] defines a stimulus set having up/down frequency sweeps starting at 500 Hz, with a duration of 250 ms, and with 2 frequency sweeps in sequence.

INTER STIMULUS INTERVAL (ISI)

The amount of silence between each frequency sweep in a sequence is defined as an inter stimulus interval, or ISI. Each stimulus set that is used to develop a trial sequence must consider how much silence is to be provided between the frequency sweeps. In one embodiment, sequences for each stimulus set are generated using the following ISI's: 1000, 900, 800, 700, 600, 500, 400, 300, 200, 150, 140, 130, 120, 110, 100, 90, 80, 70, 60, 50, 40, 30 and 20 milliseconds. For example, a stimulus set [500_80_3] with ISI of 150 would present 3 up/down frequency sweeps, starting at 500 Hz, each having a duration of 80 ms, separated from each other by 150 ms.

STIMULUS STREAM

For each trial initiated by a subject, a sequence of frequency sweeps is presented, defined by the stimulus set and the ISI. In addition, the pattern of up/down frequency sweeps over the number of frequency sweeps in a sequence is defined as the stimulus stream. The ordering of up/down sweeps within a sequence is randomized, but in one embodiment, is restricted according to the table provided above with reference to the # of sweeps in a sequence.

With the above background on stimulus sets, ISI and stimulus streams used to present trials to a subject, the methodology of using frequency sweeps within the game environment of Trog Walkers will now be described with reference to FIGS. 15 and 16.

Figure 15:
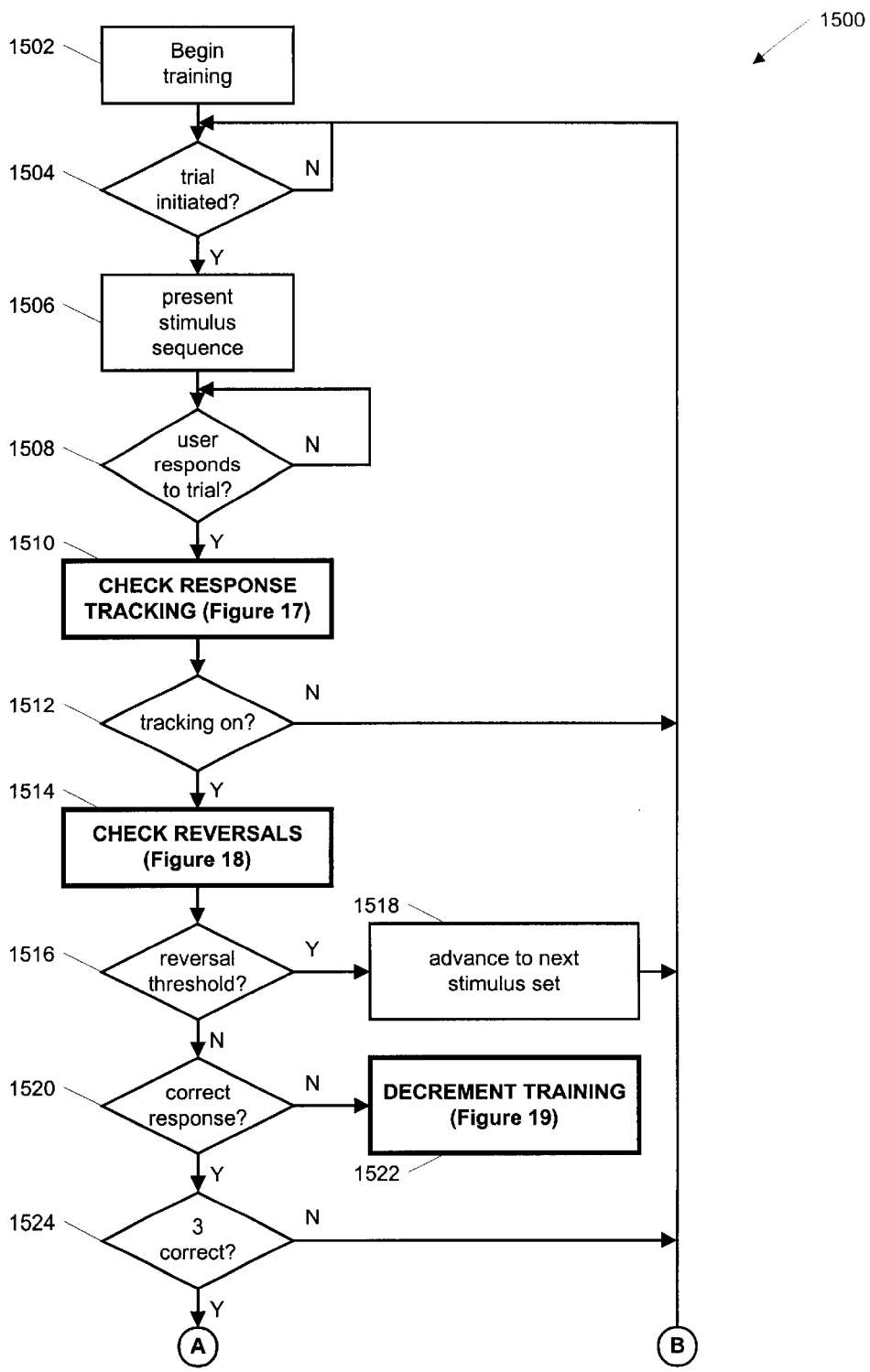
FIG. 15 is a flow chart illustrating the adaptive auditory procedures embodied in the training portion of the game Trog Walkers.
Figure 15:
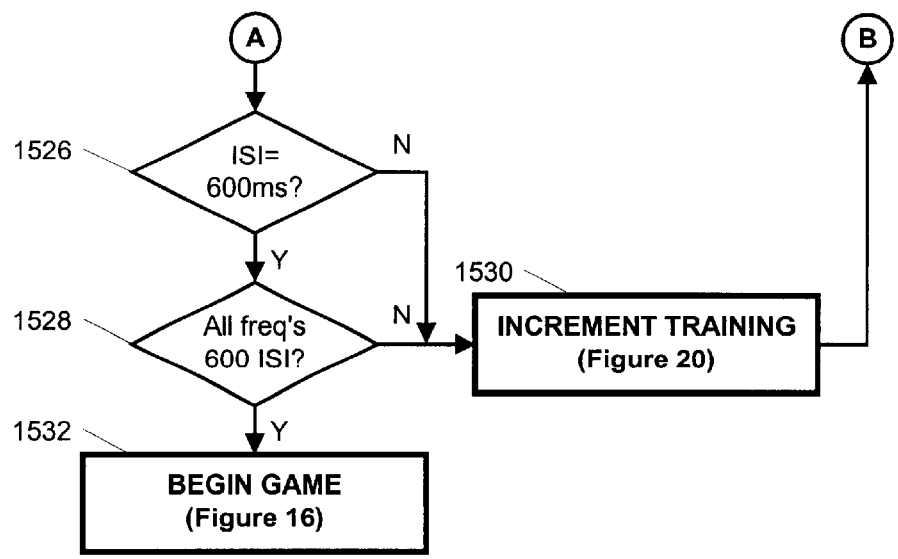

Referring first to FIG. 15, a flow chart 1500 is shown illustrating the adaptive methodology incorporated in an initial training stage of game Trog Walkers. The initial training stage teaches the subject how to play the game, and begins by presenting frequency sweeps that are easily distinguished. Training begins at block 1502 and proceeds to decision block 1504.

At decision block 1504 a determination is made as to whether the subject has initiated a trial. Recall from FIG. 10, a sequence of frequency sweeps is generated when the subject presses the trial initiation button 1020. The game remains at decision block 1504 until the button 1020 is pressed. Once it is pressed, flow proceeds to block 1506.

At block 1506, a stimulus sequence is presented. Referring to block 1540 of FIG. 15, a complete list of stimulus sets for the training portion of the game is provided. The training portion begins by opening up stimulus sets: 500_250_2, 1000_250_2, and 2000_250_2, all with an ISI of 1000 ms. The subject is first presented with a stimulus sequence of 2 up/down frequency sweeps at 500 Hz, having a duration of 250 ms each. Flow then proceeds to decision block 1508.

At decision block 1508, a determination is made as to whether the subject has responded to the trial. Referring back to FIG. 10, this corresponds to whether the subject has pressed either or both of the response buttons 1022, 1024. Once the subject responds to the trial, flow proceeds to block 1510.

At block 1510, the response provided by the subject is checked. Trog Walkers is a game that adaptively trains a subject to distinguish between up/down frequency patterns. As a subject's discrimination abilities improve, the difficulty level of the sweep sequences increases, as will be further described below. Block 1510 performs the necessary checking to prevent the program from progressing to either another stimulus set, or to a different training level, until the subject has responded correctly to 4 consecutive trials. This is particularly shown in FIG. 17 to which attention is now directed.

Figure 17:
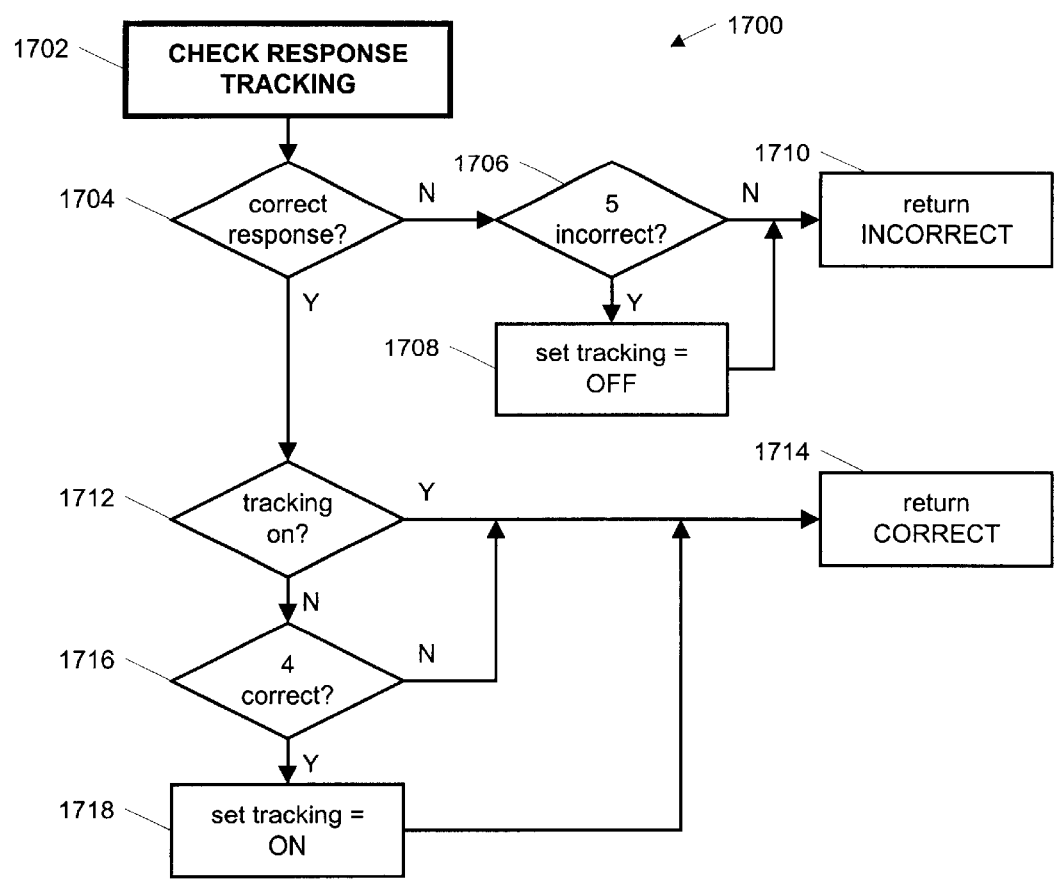
FIG. 17 is a flow chart illustrating the response tracking method according to the present invention.

FIG. 17 provides a flow chart 1700 that illustrates the response tracking according to the present invention. Flow begins at block 1702 and proceeds to decision block 1704.

At decision block 1704, a determination is made as to whether the subject's response is correct. That is, did the subject press the buttons 1022, 1024 in an order that corresponds to the up/down frequency sweeps presented by block 1506. If not, flow proceeds to decision block 1706. Otherwise, flow proceeds to decision block 1712.

At decision block 1706, a determination is made as to whether the subject has incorrectly responded to the last 5 consecutive trials. If not, then flow proceeds to block 1710 where the program records the subject's response as incorrect. Otherwise flow proceeds to block 1708.

At block 1708, response tracking is turned off. This prevents the subject from progressing further in the game until tracking is turned back on as described below. In one embodiment, it is believed that if a subject incorrectly responds to 5 or more trials, that it should not correspondingly reduce the skill level. For example, if a subject's attention wanders and yet they continue to press the buttons without attending to the listening trial, they would reduce the skill level to a level that is even easier than what was achieved on previous days. The negative consequence of this behavior is that earlier gains could be lost, simply because the subject is not paying attention. So, Trog Walkers turns response tracking off after 5 incorrect responses, and turns response tracking back on after 4 correct responses. Flow then proceeds to block 1710 where the subject's response is recorded as incorrect.

At decision block 1712, a determination is made as to whether tracking is on. If it is, then flow proceeds to block 1714 where the subject's response is recorded as correct. If tracking is not on, flow proceeds to decision block 1716.

At decision block 1716, a determination is made as to whether the subject has correctly responded to the last 4 consecutive trials. Until the subject correctly responds to 4 consecutive trials, at the beginning stimulus set, with an ISI of 1000 ms, the subject is prevented from progressing. Flow proceeds to block 1714 where the subject's response is recorded as correct, but tracking remains off. When the subject correctly responds to 4 consecutive trials, flow proceeds to block 1718.

At block 1718, tracking is turned on. Flow then proceeds to block 1714 where the subject's response is recorded as correct.

Once response tracking has been completed, by block 1510, flow proceeds to decision block 1512.

At decision block 1512, a determination is made as to whether tracking is on. Recall, tracking remains off until the subject correctly responds to 4 consecutive trials. If tracking is not on, flow proceeds back to decision block 1504, awaiting initiation of another trial. If tracking is on, however, flow proceeds to block 1514.

At block 1514, reversals are checked. In one embodiment of the invention, as the subject progresses through the different stimulus sets, and different ISI's, it is possible that s/he, within a given stimulus set, advances and retreats within a certain ISI range. Rather than continuing to train the subject within the current stimulus set, the program adapts to switch training to one of the other open stimulus sets. For example, if the subject is training at 500_250_2, and advances/retreats ISI levels a predetermined number of times, rather than continuing training at 500_250_2, a different stimulus set, say 1000_250_2 is selected. This is more completely illustrated in FIG. 18, to which attention is now directed.

Figure 18:
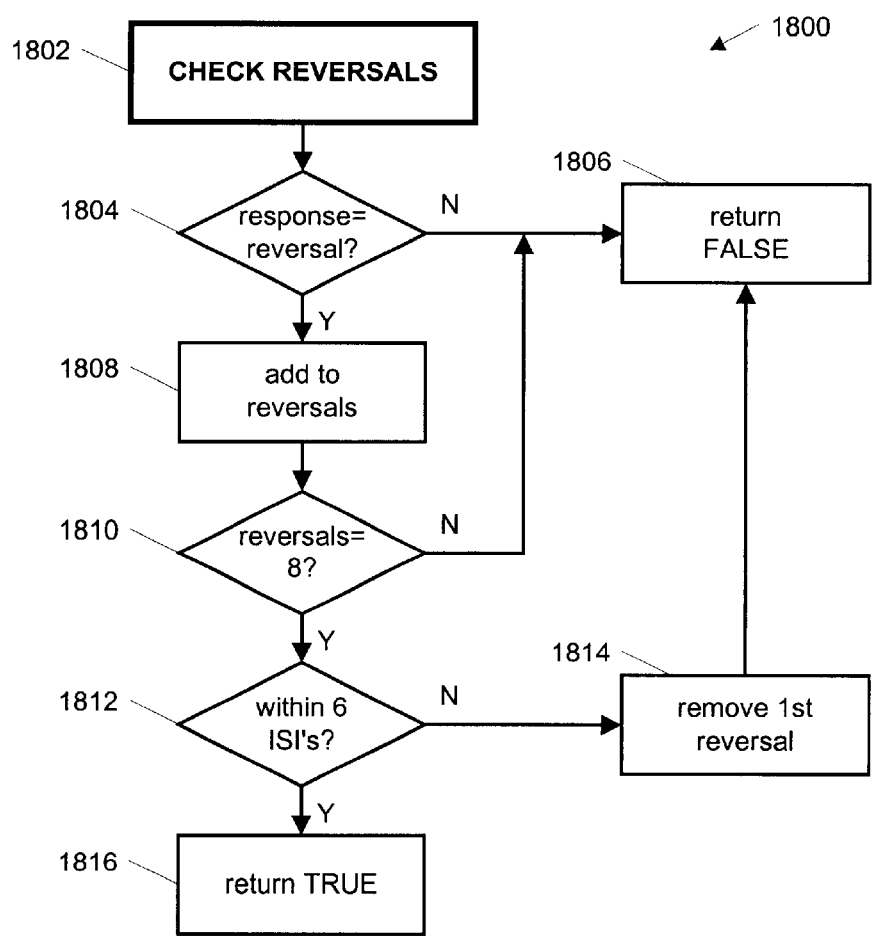
FIG. 18 is a flow chart illustrating the reversal checking method according to the present invention.

FIG. 18 provides a flow chart 1800 illustrating reversal checking according to the present invention. Reversal checking begins at block 1802 and proceeds to decision block 1804.

At decision block 1804, a determination is made as to whether the subject's response will create a reversal. As will be more fully described below, the game portion of Trog Walkers uses a 3 up, 1 down rule for level advancement. That is, when a subject correctly responds to 3 consecutive trials at a given stimulus set and ISI level, his/her skill level increases. And, when a subject incorrectly responds just once at a given stimulus set and ISI level, his/her skill level decreases. Reversal checking determines whether the most recent response will cause the subject either to advance or retreat in skill level, and whether the subject has advanced/retreated a predetermined number of times. Decision block 1804 determines if the current response will create a reversal in skill level. If not, then a reversal parameter is set to false. Otherwise, flow proceeds to block 1808.

At block 1808, the number of reversals accumulated by the subject is incremented by one. Flow then proceeds to decision block 1810.

At decision block 1810, a determination is made as to whether the subject has accumulated eight reversals. If not, flow proceeds to block 1806. However, if the subject has accumulated eight reversals, flow proceeds to decision block 1812.

At decision block 1812 a determination is made as to whether the subject as accumulated eight reversals within six ISI levels. That is, if the eight reversals are within an ISI range of six contiguous skill levels. If not, then the $1^{st}$ accumulated reversal is removed from the records. This situation occurs when there are eight accumulated reversals, but they are outside the six ISI level range. However, if the eight reversals are within six ISI skill levels, the reversal parameter is set to true.

Once reversals are check at block 1514, flow proceeds to decision block 1516.

At decision block 1516, a determination is made as to whether a reversal threshold has been met. If it has, then flow proceeds to block 1518. However, if a reversal threshold has not been met, flow proceeds to decision block 1520.

At block 1518, the program is set to advance to the next stimulus set. That is, the program adaptively moves the training to an alternative stimulus set rather than continuing to train within the existing stimulus set. For example, if the current stimulus set is 500_80_2, and the subject has had eight reversals within an ISI skill level between 900 ms and 600 ms, then the stimulus set 1000_80_2 will be selected for training. Flow then proceeds to decision block 1504 to await initiation of a trial using the new stimulus set.

At decision block 1520 a determination is made as to whether the subject provided a correct response. If not, flow proceeds to block 1522. Otherwise flow proceeds to decision block 1524.

At block 1522 the training level is decremented. That is, if the subject has not yet reached a threshold level of reversals at the current skill level, but has responded incorrectly to a trial, his/her skill level is decremented. This is particularly illustrated in FIG. 19 to which attention is now directed.

Figure 19:
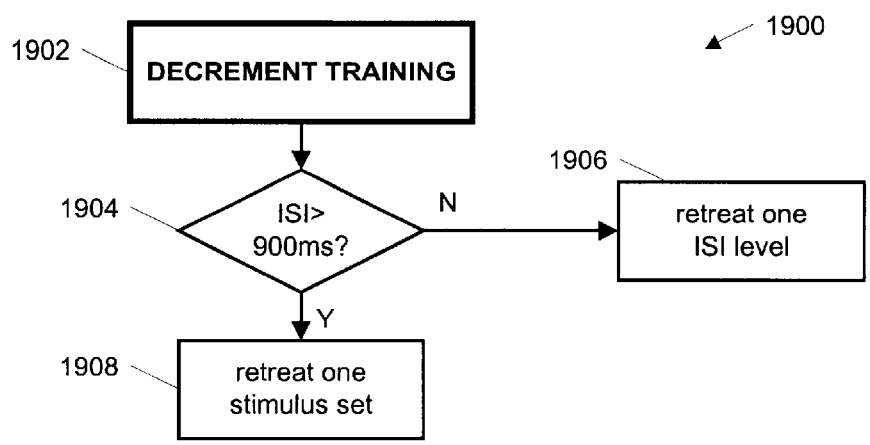
FIG. 19 is a flow chart illustrating the skill decrementing method according to the present invention.

In FIG. 19, a flow chart 1900 is provided that illustrated skill level decrementing. Flow begins at block 1902 and proceeds to decision block 1904.

At decision block 1904 a determination is made as to whether the current ISI level greater than 900 ms. In one embodiment, rather than progressively reducing the ISI within a given stimulus set, the subject is initially trained to discriminate between two frequency sweeps, all having an ISI of 1000 ms, the trials differing in the duration and frequency of the sweeps. Progression through the stimulus sets is particularly illustrated in block 1540 of FIG. 15. If the current ISI is greater than 900 ms, flow proceeds to block 1906 where the program retreats backwards one stimulus set. However, if the current ISI is less than or equal to 900 ms, flow proceeds to block 1908 where the program retreats one ISI level At decision block 1524, a determination is made as to whether the subject has correctly responded to three consecutive trials. If not, then flow proceeds back to decision block 1504 to await initiation of another trial. Otherwise, flow proceeds to decision block 1526.

At decision block 1526, a determination is made as to whether the current ISI level is 600 ms. If not, then flow proceeds to block 1530. Otherwise flow proceeds to decision block 1528.

At block 1530, the skill level for the subject is incremented. That is, if the subject has reached block 1530 it is because s/he has correctly responded to 3 consecutive trials, and is ready for advancement. Incrementation of training is particularly illustrated in FIG. 20 to which attention is now directed.

Figure 20:
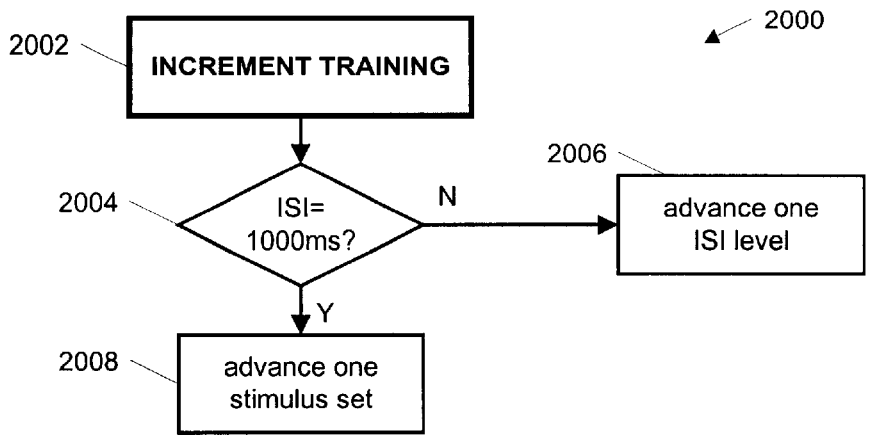
FIG. 20 is a flow chart illustrating the skill incrementing method according to the present invention.

FIG. 20 provides a flow chart 2000 illustrating incrementation of training according to the present invention. Incrementation begins at block 2002 and proceeds to decision block 2004.

At decision block 2004 a determination is made as to whether the current ISI level is 1000 ms. If so, then flow proceeds to block 2008 where the stimulus set is advanced one level. For example, if the current stimulus set is 1000_150_2, at an ISI of 1000 ms, the training increments to stimulus set 2000_150_2.

At decision block 1528, a determination is made as to whether the subject has advanced through all stimulus sets, in all frequencies, through the ISI skill level of 600 ms. If not, then flow proceeds to block 1530 where training is incremented. However, if the subject has progressed through all stimulus sets, through an ISI level of 600 ms, s/he has completed the training portion and is ready to begin the game.

Figure 16:
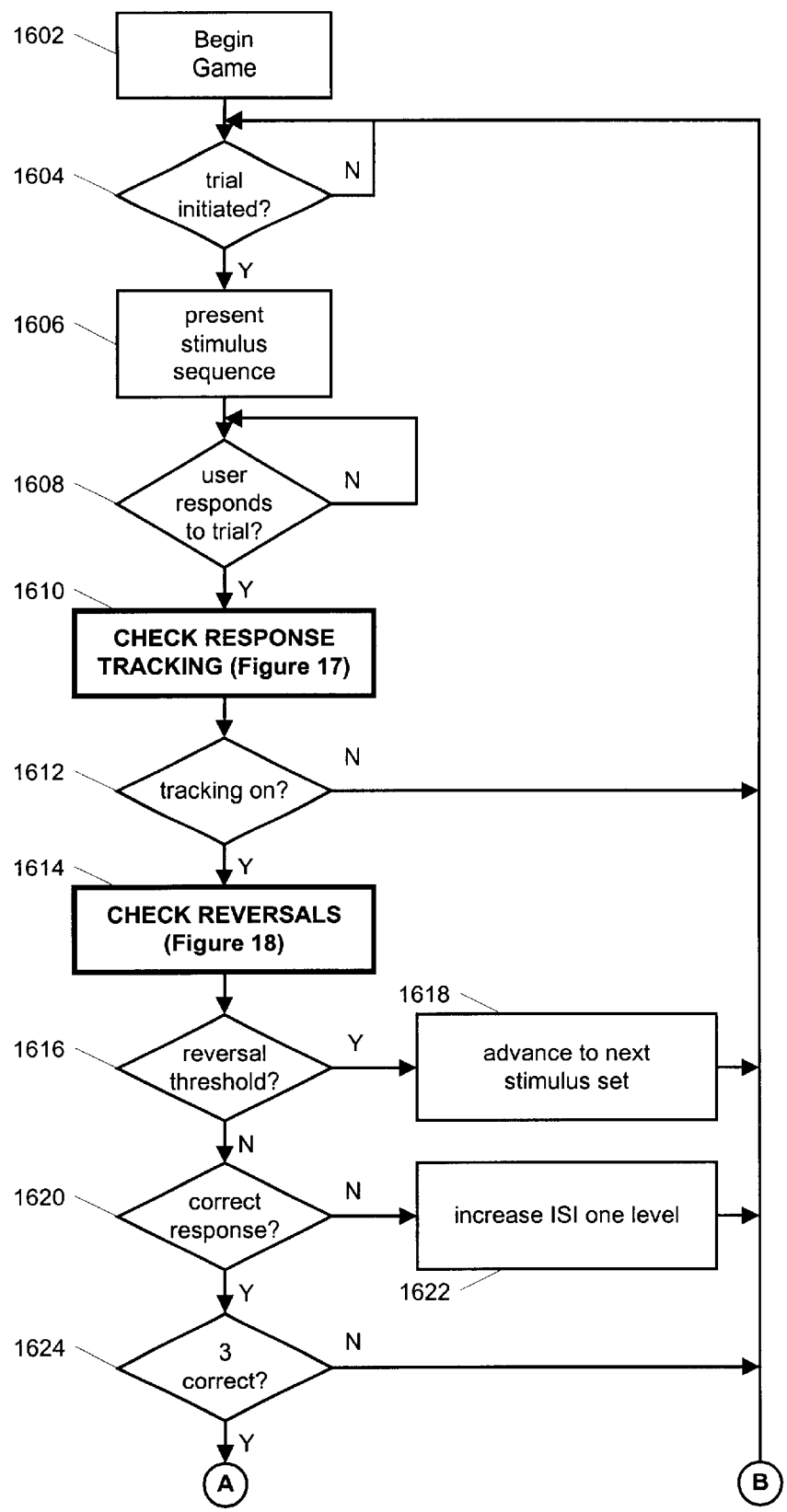
FIG. 16 is a flow chart illustrating the adaptive auditory procedures embodied in the game portion of Trog Walkers.
Figure 16:
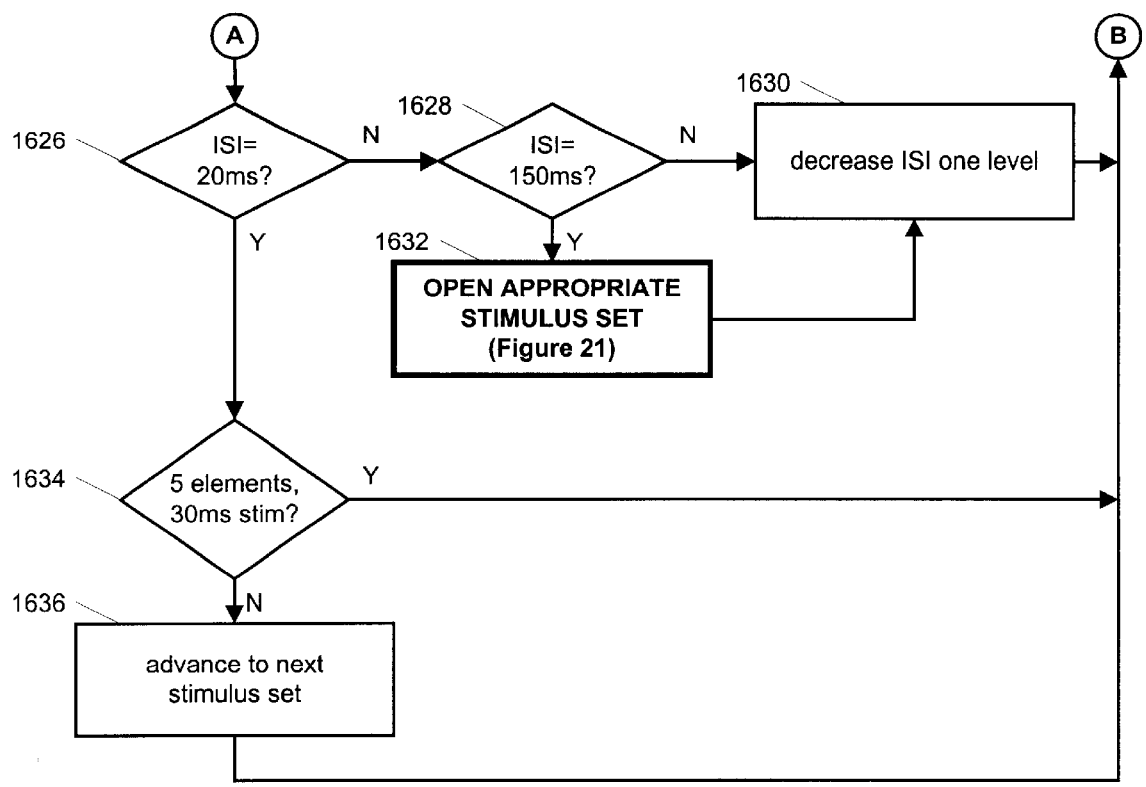

Referring now to FIG. 16, a flow chart 1600 is shown that particularly illustrates the adaptive training mechanism of Trog Walkers, once the initial training sequence of FIG. 15 has been completed. Game play begins at block 1602 and proceeds to decision block 1604.

At decision block 1604, a determination is made as to whether the subject has initiated a trial. If not, then flow remains at block 1604. However, once the subject initiates a trial, flow proceeds to block 1606.

At block 1606, the game presents a stimulus sequence to the subject. In one embodiment, the order of stimulus sequences is provided by block 1640 of FIG. 16. Game play begins with three open stimulus sets: 500_80_2, 1000_80_2, and 2000_80_2. All of these begin with an ISI of 500 ms. In contrast to the training module described above, advancement in skill is made by reducing the ISI level for a given stimulus set. That is, game play begins with stimulus set 500_80_2 at ISI 500 ms, and as the subject correctly responds to trials, training of stimulus set 500_80_2 continues until the ISI reaches 20 ms, or in the alternative, until the subject reaches a threshold. When a threshold is reached, an alternate stimulus set is selected for presentation. This will be further described below.

At decision block 1608, a determination is made as to whether the subject has responded to the trial. If not, flow remains at block 1608. Otherwise flow proceeds to block 1610.

At block 1610 response tracking is checked. This was completely described above with reference to FIG. 17. Flow then proceeds to decision block 1612.

At decision block 1612, a determination is made as to whether tracking is on. If not, flow proceeds back to decision block 1604 to await initiation of another trial. Otherwise flow proceeds to block 1614.

At block 1614 reversal checking is performed. This was completely described above with reference to FIG. 18. Flow then proceeds to decision block 1616.

At decision block 1616, a determination is made as to whether the subject has reached a reversal threshold. If so, flow proceeds to block 1618 where the next open stimulus set is selected for presentation. In one embodiment, a subject stays with a particular stimulus set, from 500 ms thru 20 ms unless s/he reaches a threshold. If a threshold is reached, the threshold level is stored away for the particular stimulus set, and an alternate stimulus set, from the group of open stimulus sets, is selected for training.

Initially, game play begins with three open stimulus sets, as shown in block 1640. As a subject advances past the 150 ms ISI threshold for a given stimulus set, two additional stimulus sets are opened. The first additional stimulus set increases the number of frequency sweeps for the given frequency and duration. For example if a subject advances past 500_80_2 at 150 ms, a new stimulus set of 500_80_3 is opened (at 500 ms). In addition, a second additional stimulus set is opened with a shorter sweep duration of 30 ms (500_30_2), also with an ISI of 500 ms. When a subject reaches a threshold, s/he is provided with a sequence from one of the alternate open stimulus sets.

The stimulus sets remain open until the subject progress thru the 20 ms ISI level for each open set. Thus, new stimulus sets are opened when a subject advances past 150 ms, and are closed when a subject completes a set at an ISI of 20 ms.

The program maintains a history of open stimulus sets, and the ISI level reached that last time training occurred for that stimulus set. The next time a subject begins game play, a selection is made among the open stimulus sets for presentation to the subject. However, the program reads the last training level, or threshold level, obtained by the subject for the selected stimulus set, and begins training with an ISI skill level that is 5 levels back from that previously reached. This allows a subject to start training at a skill level that is more easily succeeded, rather than starting him/her at their previous threshold.

At decision block 1620, a determination is made as to whether the subject correctly responded to the trial. If not, flow proceeds to block 1622 where the ISI is reduced one level. Otherwise, flow proceeds to decision block 1624.

At decision block 1624, a determination is made as to whether the subject has correctly responded to the last 3 trials. If not, flow proceeds back to decision block 1604 to await initiation of another trial. Otherwise, flow proceeds to decision block 1626.

At decision block 1626, a determination is made as to whether the current ISI level is 20 ms. As explained above, once a subject reaches the 20 ms ISI for a given stimulus set, that stimulus set is closed out, and an additional stimulus set is opened. If the current ISI level is 20 ms, flow proceeds to decision block 1634. Otherwise, flow proceeds to decision block 1628.

At decision block 1628, a determination is made as to whether the current ISI is 150 ms. If it is not, flow proceeds to block 1630 where the ISI level is decreased, and flow proceeds back to decision block 1604 to await initiation of another trial. However, if the current ISI is 150 ms, flow proceeds to block 1632.

At block 1632, the program opens all appropriate stimulus sets. This is particularly illustrated in FIG. 21, to which attention is now directed.

Figure 21:
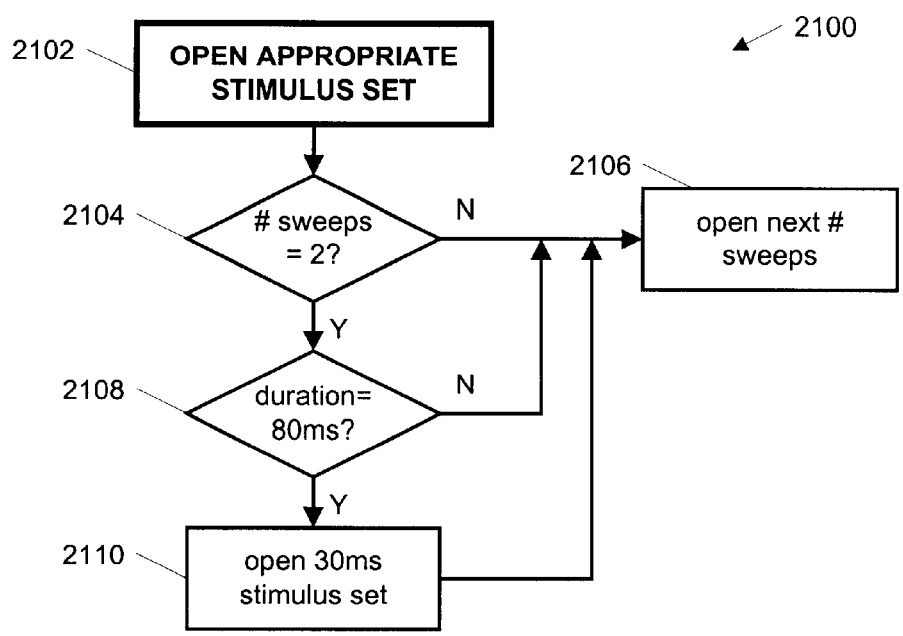
FIG. 21 is a flow chart illustrating the method for adaptively opening selected stimulus sets to be used in training, according to the present invention.

FIG. 21 provides a flow chart 2100 that illustrates how the program adaptively opens additional stimulus sets. Flow begins at block 2102 and proceeds to decision block 2104.

At decision block 2104, a determination is made as to whether the number of current sweeps for the current stimulus set is 2. If not, then flow proceeds to block 2106 where an additional stimulus set is opened that increases the number of sweeps for the current stimulus set. If the current number of sweeps is 2, then flow proceeds to decision block 2108.

At decision block 2108, a determination is made as to whether the sweep duration for the current stimulus set is 80 ms. If not, then flow proceeds to block 2106 where the number of sweeps is increased. Otherwise, flow proceeds to block 2110.

At block 2110, an additional stimulus set is opened that reduces the sweep duration to 30 ms, at the current frequency, beginning with a sweep number of 2. Flow then proceeds to block 2106 where a single additional stimulus set is opened that increases the number of sweeps for the stimulus set corresponding to the one that caused entry into block 1632.

At block 1632, once the appropriate stimulus sets have been opened, flow proceeds to block 1630 where the ISI is decreased for the current stimulus set by one level. Flow then proceeds back to decision block 1604 for initiation of another trial.

At decision block 1634, a determination is made as to whether the current stimulus set includes 5 sweep frequencies of 30 ms duration. If not, then flow proceeds back to decision block 1604 to await initiation of another trial. Otherwise flow proceeds to block 1636.

At block 1636, the subject has proceeded from through all stimulus sets, at all ISI's, for a given frequency. The program therefore advances the subject through all of the open stimulus sets.

The above description of the present invention provides an understanding of a racing game environment that adaptively trains a subject to discriminate between upward and downward going frequency sweeps, at a variety of frequencies, having a variety of durations, separated by a variety of ISI's, and with a varying number of sweeps in each trial. The particular frequencies used in the training, the rate of the frequency sweeps, the duration of the sweeps, the separation of the sweeps, the number of sweeps within a trial, and the adaptive methodology used to advance a subject to the point of distinguishing frequency sweeps common in spoken language, are extremely effective at retraining the auditory processing capabilities of the subject. However, they are not considered exhaustive. It is entirely within the scope of this invention to utilize alternative frequencies, within the range of human hearing, having different sweep rates, durations, and ISI's, without departing from the novel aspects of the present invention.

Moreover, the background of Trog Walkers is that of a running race. This game environment is simply to maintain the interest of the subject while they progress through repetitive, and often tedious neurological training exercises. The present invention anticipates that alternative gaming environments may be used to further entertain the subject, while still incorporating the methodology described herein.

Although the present invention and its objects, features, and advantages have been described in detail, other embodiments are encompassed by the invention, could be used.

Finally, the Trog Walkers program has been shown for execution on a personal computer, connected to a central server. However, as technology advances, it is envisioned that the program could be executed either by a diskless computer attached to a server, by a handheld processing device, such as a laptop, or eventually by a palmtop device such as a Nintendo GameBoy. As long as the graphical images and auditory prompts can be presented in a timely fashion, and with high quality, the nature of the device used to present the material is irrelevant.

Those skilled in the art should appreciate that they can readily use the disclosed conception and specific embodiments as a basis for designing or modifying other structures for carrying out the same purposes of the present invention without departing from the spirit and scope of the invention as defined by the appended claims.

We claim:

1. A method for training a subject to process and distinguish the order of upward and downward going frequency sweeps of frequency (f), separated by a predetermined inter stimulus interval (ISI), the method comprising:
   presenting a sequence containing a plurality of frequency sweeps that are separated by the ISI to a subject for the order identification, the sequence having at least one upward going sweep and at least one downward going sweep;
   requiring the subject to signal identification of the order of the plurality of frequency sweeps presented in the sequence; and
   after the subject correctly identifies the order of the plurality of frequency sweeps in a plurality of presented sequences, increasing the number of frequency sweeps in the sequence.

2. The method for training a subject, as recited in claim 1, wherein the frequency (f) is within a range of 70–5000 hertz.

3. The method for training a subject, as recited in claim 1, wherein the ISI is within the range of 20–1000 milliseconds.

4. The method for training a subject, as recited in claim 1, wherein the sequence comprises a combination of upward and downward going frequency sweeps.

5. The method for training a subject, as recited in claim 1, wherein the subject signals identification of the order of the plurality of frequency sweeps presented in the sequence by selecting buttons on a computer display, that correspond to upward and downward going frequency sweeps.

6. The method for training a subject, as recited in claim 5, wherein correct identification of the order of the plurality of frequency sweeps exists when the subject selects the corresponding buttons according to the order of the plurality of frequency sweeps.

7. The method for training a subject, as recited in claim 1, further comprising repeating, before increasing the number of frequency sweeps in the sequence, presenting a sequence containing a plurality of frequency sweeps that are separated by the ISI to the subject for the order identification and requiring the subject to signal identification of the order of the plurality of frequency sweeps presented in the sequence a predetermined number of times.

8. The method for training a subject, as recited in claim 1, further comprising:
   after the subject correctly identifies the order of the plurality of frequency sweeps in a plurality of presented sequences, changing the frequency (f).

9. The method for training a subject, as recited in claim 1, wherein the upward and downward going frequency sweeps have a duration (d).

10. The method for training a subject, as recited in claim 9, further comprising:
    after the subject correctly identifies the order of the plurality of frequency sweeps in a plurality of presented sequences, reducing the duration.

11. The method for training a subject, as recited in claim 9, wherein if the subject incorrectly identifies the order of the plurality of frequency sweeps in a plurality of presented sequences, increasing the duration.

12. The method for training a subject, as recited in claim 9, wherein if the subject incorrectly identifies the order of the plurality of frequency sweeps in a plurality of presented sequences, increasing the ISI.

13. The method for training a subject, as recited in claim 9, wherein the duration is within the range of 20–250 milliseconds.

* * * * *